(12) United States Patent
Vaisvila et al.

(10) Patent No.: US 10,155,939 B1
(45) Date of Patent: Dec. 18, 2018

(54) METHOD FOR PERFORMING MULTIPLE ENZYME REACTIONS IN A SINGLE TUBE

(71) Applicant: New England Biolabs, Inc., Ipswich, MA (US)

(72) Inventors: Romualdas Vaisvila, Ipswich, MA (US); Lauren Higgins, Rockport, MA (US); Ashley Luck, Kensington, NH (US)

(73) Assignee: New England Biolabs, Inc., Ipswich, MA (US)

( * ) Notice: Subject to any disclaimer, the term of this patent is extended or adjusted under 35 U.S.C. 154(b) by 0 days.

(21) Appl. No.: 15/623,756

(22) Filed: Jun. 15, 2017

(51) Int. Cl.
| | |
|---|---|
| *C12N 9/88* | (2006.01) |
| *C12N 15/10* | (2006.01) |
| *C07H 19/073* | (2006.01) |
| *C12N 9/22* | (2006.01) |
| *C12N 15/09* | (2006.01) |
| *C11D 3/12* | (2006.01) |
| *C12N 9/00* | (2006.01) |
| *C12Q 1/52* | (2006.01) |

(52) U.S. Cl.
CPC ......... *C12N 15/102* (2013.01); *C07H 19/073* (2013.01); *C12N 9/22* (2013.01); *C12N 15/09* (2013.01); *C11D 3/122* (2013.01); *C12N 9/93* (2013.01); *C12Q 1/52* (2013.01)

(58) Field of Classification Search
None
See application file for complete search history.

(56) References Cited

U.S. PATENT DOCUMENTS

| | | | | |
|---|---|---|---|---|
| 5,418,149 A | * | 5/1995 | Gelfand | C12N 9/1276 435/6.12 |
| 7,435,572 B2 | | 10/2008 | Bitinaite | |
| 8,420,319 B2 | | 4/2013 | Mikawa et al. | |
| 9,121,061 B2 | | 9/2015 | Vaisvila et al. | |
| 2016/0257985 A1 | * | 9/2016 | Kamberov | C12Q 1/6848 |

FOREIGN PATENT DOCUMENTS

| | | |
|---|---|---|
| WO | WO 2013/138644 | 9/2013 |
| WO | WO 2017/075436 | 5/2017 |

OTHER PUBLICATIONS

Ehrich, Nucl. Acids Res. 35:e29 (2007).
Stenglein, Nature Structural & Molecular Biology, 17: 222-229 (2010).
Margulies, et al., Nature 2005 437: 376-80.
Ronaghi, et al., Analytical Biochemistry, 1996 242: 84-9.
Shendure, Science 2005 309: 1728.
Imelfort, et al., Brief Bioinform. 2009 10:609-18.
Fox, et al., Methods Mol Biol. 2009;553:79-108.
Appleby, et al., Methods Mol Biol. 2009;513:19-39.
Morozova, Genomics, 2008 92:255-64.
Soni, et al., Clin Chem 53: 1996-2001 2007.
Adey, Genome Res. 2014 24: 2041-9.
Amini, Nat Genet. 2014 46: 1343-9.
Carbson, Nucleic Acids Res. 2013 41:e112.
Krueger, et al. Bioinformatics 27, No. 11 (2011): 1571-1572.
New England Biolabs Catalog 2015-2016, p. 124.
English, PLoS One, 2012 7: e47768.

* cited by examiner

*Primary Examiner* — Hope Robinson
(74) *Attorney, Agent, or Firm* — New England Biolabs, Inc.; Harriet M. Strimpel

(57) ABSTRACT

Among other things, a method for performing multiple enzyme reactions in a single tube is provided. In some embodiments, the method may comprise producing a reaction mix comprising a thermolabile UDG, an AP lyase and DNA fragments that comprise one or more uracil residues, incubating the reaction mix at a relatively low temperature to cleave fragments at the one or more uracil residues, raising the temperature of the reaction mix to a relatively high temperature to inactivate the thermolabile UDG; and deaminating the fragments, thereby converting any cytosine in the fragments of DNA to uracil.

12 Claims, 7 Drawing Sheets

(4 of 7 Drawing Sheet(s) Filed in Color)

Specification includes a Sequence Listing.

FIG. 1A

5' FAM-GATTTCATTTTTATTUATAACTTTACTTATATTG-3' (SEQ ID NO:1)
3'     -CTAAAGTAAAAATAAATATTGAAATGAATATAAC-5'  (SEQ ID NO:2)

FIG. 1B

5' FAM-CGGAATTCGTCTAGGTTTGAGGTUGACATCGGATCCATGGTACCTCGAGGGCAATGTCTA-dTFAM-3' (SEQ ID NO:3)
3'     -GCCTTAAGCAGATCCAAACTCCAACTGTAGCCTAGGTACCATGGAGCTCCCGTTACAGAT-        5' (SEQ ID NO:4)

METHOD FOR PERFORMING MULTIPLE ENZYME REACTIONS IN A SINGLE TUBE

BACKGROUND

DNA can be specifically cleaved at nucleotide residues that contain uracil by treatment with uracil DNA glycosylase (UDG) and an AP-lyase. The UDG catalyzes the excision of a uracil base, forming an abasic (apyrimidinic) site while leaving the phosphodiester backbone intact. The AP-lyase breaks the phosphodiester backbone at the 3' and 5' sides of the abasic site to release a base-free deoxyribose. This reaction has conventionally been done using the UDG and Endonuclease VIII (Endo VIII) enzymes from E. coli.

Cleavage of uracil has been exploited to cleave adaptors in preparing samples for sequencing. This workflow typically involves ligating adaptors that contain uracil residues onto nucleic acid fragments, cleaving the adaptors using UDG and AP-lyase (typically in a single reaction using a mix of enzymes), amplifying the fragments using primers that hybridize to the adaptors, and then sequencing the fragments. In some next generation sequencing applications, nucleotides in the fragments are covalently modified after cleavage of the adaptors.

Epigenetic genome markers can be sequenced using for example, bisulfite sequencing. The fragments are deaminated cytosines (C) (but not methylcytosines) are converted to uracil (U). The sequences of the deaminated fragments (or their amplification products) can be analyzed to identify the positions of cytosines and methylcytosines in the original fragments. Unfortunately, conventional uracil-specific cleavage reagents (e.g., E. coli UDG and Endo VIII) can cause non-specific degradation during extended incubation times, or even under conditions that should have inactivated those reagents.

SUMMARY

Provided herein, among other things, is a method for subjecting a DNA sample to multiple enzyme reactions (e.g., a uracil-specific cleavage reaction and a deamination reaction) in a way that avoids potential problems caused by incomplete inactivation of the uracil-specific cleavage reagents. In some conventional methods, the UDG used in the initial step of the method (e.g., in the uracil-specific cleavage step) can be partially active after the second enzyme treatment step (i.e., after the deamination step) and, as such, can produce sugarless residues and/or nicks at the deaminated sites. Because molecules that contain sugarless residues and/or nicks cannot be copied, they cannot be sequenced. These molecules are often referred to as "dropouts" and are a source of bias in some DNA methylation studies. The problem is exacerbated by the fact that many of the molecules under study (e.g., eukaryotic genomic DNA or plasmids, for example) contain many more C's (which are converted to U in the deamination step) than modified C's (which are not converted to uracil in the deamination step). As such, even a small amount of UDG carry-over can potentially cause significant bias. The use of a thermolabile UDG in the initial step of such methods solves this problem.

In general in one aspect, a method is provided for performing multiple enzyme reactions in a single tube: where the method includes: (a) producing a reaction mix comprising a thermolabile UDG, an AP lyase and fragments of genomic or plasmid DNA that comprise one or more uracil residues; (b) incubating the reaction mix at a temperature of below 40° C. to cleave the genomic or plasmid DNA fragments at the one or more uracil residues; (c) raising the temperature of the reaction mix to at least 50° C. for a period of time to inactivate the thermolabile UDG; and (d) deaminating the fragments of genomic or plasmid DNA after inactivating thermolabile UDG, thereby converting any cytosine in the fragments of DNA to uracil.

In one aspect, the fragments of genomic or plasmid DNA include an oligonucleotide, wherein the oligonucleotide contain the one or more uracil residues. In one example, the oligonucleotide is an adapter such as a loop adapter, ligated to at least one end of the genomic or plasmid fragments.

In one aspect, AP lyase is also thermolabile such as Endonuclease III (Endo III). In another aspect, in (d) the deaminating is performed using a deaminase enzyme, for example, a deaminase enzyme that has at least 90% sequence identity with SEQ ID NO:1 (APOBEC). Alternatively, deamination may be performed by sodium bisulfite treatment.

In one aspect, the method described above includes (e) amplifying the fragments of genomic or plasmid DNA. Further method steps may include: sequencing the amplification product and optionally identifying the sites of methylcytosines and/or hydroxymethylcytosine residues in the fragments of genomic or plasmid DNA.

In general in one aspect, a composition is provided that includes a thermolabile UDG, an AP lyase and fragments of genomic or plasmid DNA that include an oligonucleotide such as is a loop adaptor that is ligated to at least one end of the fragments, where the oligonucleotide contains one or more uracil residues.

In general in one aspect, a kit is provided that includes a thermolabile UDG, an AP lyase and an oligonucleotide containing one or more uracil residues ligated to at least at one end of the fragments. The kit may also include an adaptor such as a loop adaptor. The kit may include a deaminase.

In general in one aspect, a method is provided for ligating an adaptor onto a fragment of genomic or plasmid DNA, that includes: (a) producing a reaction mix comprising a thermostable UDG, a thermostable AP lyase, ligase, fragments of genomic or plasmid DNA, and an adapter containing one or more uracil residues; (b) incubating the reaction mix at a temperature of below 37° C. to ligate the adapter onto at least one end of the fragments of genomic or plasmid DNA; (c) raising the temperature of the reaction mix to at least 50° C. for a period of time in order to activate the thermostable UDG and thermostable AP lyase, thereby cleaving the adapter at the one or more uracil residues.

In one aspect, the method includes deaminating the fragments of genomic or plasmid DNA, thereby converting any cytosine in the fragments of DNA to uracil. In one aspect, the thermostable UDG is Afu UDG and the thermostable AP lyase is Tth Endonuclease IV (Endo IV).

In general in one aspect, a composition is provided that includes: a thermostable UDG, a thermostable AP lyase, ligase, fragments of genomic or plasmid DNA, and an adapter containing one or more uracil residues. In one aspect, a deaminase is included.

In general, in one aspect, a method is provided that includes the steps of producing a reaction mix comprising UDG, Endo III and fragments of genomic or plasmid DNA that comprise an adapter containing one or more uracil residues, wherein the adaptor is ligated to at least one end of the fragment; and incubating the reaction mix to cleave the adaptor at the one or more uracil residues. In one aspect, the reaction mix has less than 100 genome equivalents of genomic DNA.

BRIEF DESCRIPTION OF THE FIGURES

The patent or application file contains at least one figure executed in color. Copies of this patent or application publication with color figures will be provided by the Office upon request and payment of necessary fee.

The skilled artisan will understand that the drawings, described below, are for illustration purposes only. The drawings are not intended to limit the scope of the present teachings in any way.

FIG. 1A shows the sequence of a 34-bp oligonucleotide duplex used to assay the activity of artificial nicking agents. The top strand of the duplex is fluorescently labeled on the 5' and contains a single uracil (U) at the $16^{th}$ position. The bottom strand of the heteroduplex contains a adenine across from the position corresponding to dU. SEQ ID NO: 1 and SEQ ID NO:2.

FIG. 1B shows the sequence of a 60-bp oligonucleotide duplex used to assay the activity of thermostable artificial nicking agents. The top strand of the duplex is fluorescently labeled on both the 5' and 3' ends and contains a single U at the $24^{th}$ position. The bottom strand of the heteroduplex contains a adenine across from the position corresponding to dU. SEQ ID NO: 3 and SEQ ID NO:4.

FIG. 3A shows a schematic diagram of a method useful for detection of 5-methylcytosines in whole mammalian genome. DNA was sheared to 250-400 bp, then DNA ends were repaired, dA tailed and a NEBNext modified loop adaptor ligated. To avoid thermostable UDG carry over, the thermolabile nicking agent was used to cut a NEBNext modified loop adaptor.

FIG. 3B shows a schematic diagram of a method useful for detection of 5-hydroxymethylcytosines in whole mammalian genome. DNA was sheared to 250-400 bp, then 5-hydroxymethylcytosines were glucosylated with T4-BGT enzyme, DNA ends repaired, dA tailed and a NEBNext modified loop adaptor ligated. To avoid thermostable UDG carry over, the thermolabile nicking agent was used to cut a NEBNext modified loop adaptor.

FIG. 6A shows a schematic diagram of the NEBNext DNA Ultra II workflow. The standard nicking agent is active at 20° C., so that the NEBNext adaptor ligation must first be incubated for 15 minutes at 20° C. prior to the addition of the nicking agent followed by incubation at 37° C. in order to cleave the dU-containing NEBNext adaptors in preparation for library sequencing.

FIG. 6B shows a schematic diagram of a modified NEBNext DNA Ultra II workflow in which the NEBNext adaptor ligation step has been combined with adaptor cleavage by using a thermostable nicking agent. Due to the inactivity of the thermostable nicking agent at 20° C., a single reaction mix can contain the NEBNext adaptor ligase and nicking agent. The reaction mix is first incubated for 15 minutes at 20° C. for ligation followed by incubation at 65° C. for 15 minutes in order to cleave the dU-containing NEBNext adaptors in preparation for library sequencing.

DETAILED DESCRIPTION

Figure 2:
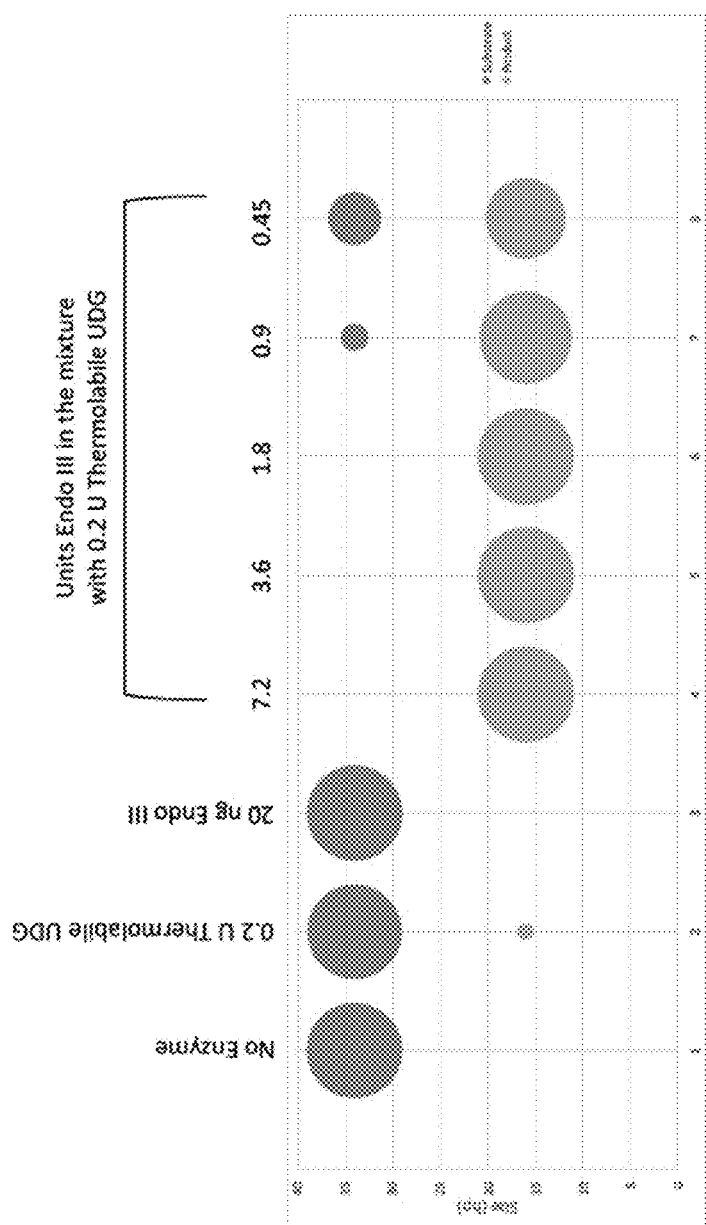
FIG. 2 shows results of assays obtained using a thermolabile UDG (Antarctic UDG) and *E. coli* Endo III. In this assay, varying amount of Endo III glycosylase/AP lyase is mixed with a thermolabile UDG glycosylase, and the mixes are tested. The assay utilizes a substrate having a sequence shown in FIG. 1A. 2-fold serially diluted amounts of Endo III varying in the range from 7.2-0.45 U were pre-mixed with 0.2 unit of thermolabile UDG glycosylase and assayed for complete nicking of 10 pmol of substrate. Lane 1 (on the far left) is a control showing the substrate without enzyme treatment. Neither Thermolabile UDG alone (shown in lane 2, second from the left) or Endo III alone (shown in lane 3, third from the left) is capable of significantly nicking the substrate containing uracil, but the mixtures containing 0.2 units of thermolabile UDG and at least 1.8 U of Endo III yield complete nicking of 10 pmol of substrate (lanes 4-6). Mixtures containing 0.9 U of Endo III or less are only partially digested (lanes 7-8). These data show that in order to obtain complete digestion under the conditions used, the Endo III:thermolabile UDG unit ratio should be at least about 1 (Endo III): 0.2 (thermolabile UDG), i.e., 5:1. UDG from *E. coli* is partially but not completely heat inactivatable so that Antarctic UDG is preferable.

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

The term "nucleic acid sample," as used herein, denotes a sample containing nucleic acids. Nucleic acid samples used herein may be complex in that they contain multiple different molecules that contain sequences. Genomic DNA samples from a eukaryote, e.g., a mammal (e.g., mouse or human) are types of complex samples. Complex samples may have more than about $10^2$, $10^3$, $10^4$, $10^5$, $10^6$ or $10^7$, $10^8$, $10^9$ or $10^{10}$ different nucleic acid molecules. A DNA target may originate from any source such as genomic DNA, or plasmid. Any sample containing nucleic acid, e.g., genomic DNA from tissue culture cells or a sample of tissue, may be employed herein.

The term "mixture" as used herein, refers to a combination of elements, that are interspersed and not in any particular order. A mixture is heterogeneous and not spatially separable into its different constituents. Examples of mixtures of elements include a number of different elements that are dissolved in the same aqueous solution and a number of different elements attached to a solid support at random positions (i.e., in no particular order).

As used herein, the term "buffering agent", refers to an agent that allows a solution to resist changes in pH when acid or alkali is added to the solution. Examples of suitable non-naturally occurring buffering agents that may be used in the compositions, kits, and methods of the invention include, for example, Tris, HEPES, TAPS, MOPS, tricine, or MES.

The term "non-naturally occurring" refers to a composition that does not exist in nature.

Any protein described herein may be non-naturally occurring, where the term "non-naturally occurring" refers to a protein that has an amino acid sequence and/or a post-translational modification pattern that is different to the protein in its natural state. For example, a non-naturally occurring protein may have one or more amino acid substitutions, deletions or insertions at the N-terminus, the C-terminus and/or between the N- and C-termini of the protein. A "non-naturally occurring" protein may have an amino acid sequence that is different from a naturally occurring amino acid sequence (i.e., having less than 100% sequence identity to the amino acid sequence of a naturally occurring protein) but that is at least 80%, at least 85%, at least 90%, at least 95%, at least 97%, at least 98% or at least 99% identical to the naturally occurring amino acid sequence. In certain cases, a non-naturally occurring protein may contain an N-terminal methionine or may lack one or more post-translational modifications (e.g., glycosylation, phosphorylation, etc.) if it is produced by a different (e.g., bacterial) cell. A "mutant" protein may have one or more amino acid substitutions relative to a wild-type protein and a "fusion" protein may have one or exogenous domains added to the N-terminus, C-terminus, and or the middle portion of the protein.

In the context of a nucleic acid, the term "non-naturally occurring" refers to a NA that contains: a) a sequence of nucleotides that is different from a nucleic acid in its natural state (i.e. having less than 100% sequence identity to a naturally occurring NA sequence), b) one or more non-naturally occurring nucleotide monomers (which may result in a non-natural backbone or sugar that is not G, A, T or C) and/or C) may contain one or more other modifications (e.g., an added label or other moiety) to the 5'-end, the 3' end, and/or between the 5'- and 3'-ends of the NA.

In the context of a composition, the term "non-naturally occurring" refers to: a) a combination of components that are not combined by nature, e.g., because they are at different locations, in different cells or different cell compartments; b) a combination of components that have relative concentrations that are not found in nature; c) a combination that lacks something that is usually associated with one of the components in nature; d) a combination that is in a form that is not found in nature, e.g., dried, freeze dried, crystalline, aqueous; and/or e) a combination that contains a component that is not found in nature. For example, a preparation may contain a "non-naturally occurring" buffering agent (e.g., Tris, HEPES, TAPS, MOPS, tricine or MES), a detergent, a dye, a reaction enhancer or inhibitor, an oxidizing agent, a reducing agent, a solvent or a preservative that is not found in nature.

As used herein, the term "composition" refers to a combination of reagents that may contain other reagents, e.g., glycerol, salt, dNTPs, etc., in addition to those listed. A composition may be in any form, e.g., aqueous or lyophilized, and may be at any state (e.g., frozen or in liquid form).

As used herein, the term "location" refers to the position of a nucleotide in an identified strand in a nucleic acid molecule.

The term "oligonucleotide" as used herein denotes a single-stranded multimer of nucleotides from about 2 to 200 nucleotides, up to 500 nucleotides in length. Oligonucleotides may be synthetic or may be made enzymatically, and, in some embodiments, are 30 to 150 nucleotides in length. Oligonucleotides may contain ribonucleotide monomers (i.e., may be oligoribonucleotides) or deoxyribonucleotide monomers, or both ribonucleotide monomers and deoxyribonucleotide monomers. An oligonucleotide may be 10 to 20, 21 to 30, 31 to 40, 41 to 50, 51 to 60, 61 to 70, 71 to 80, 80 to 100, 100 to 150 or 150 to 200 nucleotides in length, for example.

The terms "determining," "measuring," "evaluating," "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

As used herein, the term "cytidine deaminase" refers to an enzyme that is capable of deaminating C and methylcytosine (mC).

The term "sequencing," as used herein, refers to a method by which the identity of at least 10 consecutive nucleotides (e.g., the identity of at least 20, at least 50, at least 100 or at least 200 or more consecutive nucleotides) of a polynucleotide is obtained.

A "plurality" contains at least 2 members. In certain cases, a plurality may have at least 2, at least 5, at least 10, at least 100, at least 100, at least 10,000, at least 100,000, at least $10^6$, at least $10^7$, at least $10^8$ or at least $10^9$ or more members.

The terms "next generation sequencing" or "high-throughput sequencing", as used herein, refer to the so-called parallelized sequencing-by-synthesis or sequencing-by-ligation platforms currently employed by Illumina, Life Technologies, and Roche, etc. Next generation sequencing methods may also include Nanopore sequencing methods such as that commercialized by Oxford Nanopore Technologies, electronic-detection based methods such as Ion Torrent technology commercialized by Life Technologies, or single-molecule fluorescence-based methods such as that commercialized by Pacific Biosciences.

The term "thermolabile" refers to an enzyme that is fully active at a temperate in the range of 15° C. to 30° C. but has no detectable activity after being incubated at an elevated temperature, e.g., a temperate of at least 50° C., for a period of time, e.g., at least 5 minutes or at least 10 minutes.

The term "thermostable" refers to an enzyme that is not significantly active at a temperate in the range of 15° C. to 30° C. and is relatively stable and active activity at an elevated temperature, e.g., a temperature in the range of 50° C. to 72° C.

The terms "uracil DNA glycosylase" or "UDG" refer to an enzyme that catalyzes the release of free uracil from uracil-containing DNA. UDG can efficiently hydrolyze uracil from single-stranded or double-stranded DNA. One unit of UDG is defined as the amount of enzyme that catalyzes the release of 60 pmol of uracil per minute from double-stranded, uracil-containing DNA. Activity is measured by release of [$^3$H]-uracil in a 50 μl reaction containing 0.2 μg DNA ($10^4$–$10^5$ cpm/μg) in 30 minutes at 37° C.

The term "AP lyase" refers to an enzyme that catalyzes the chemical reaction of the cleavage of the C3'-O—P bond 3' from the apurinic or apyrimidinic site in DNA via beta-elimination reaction, leaving a 3'-terminal unsaturated sugar and a product with a terminal 5'-phosphate. This enzyme can also be referred to as DNA-(apurinic or apyrimidinic site) lyase, or DNA-(apurinic or apyrimidinic site) 5'-phosphomonoester-lyase (systematic name), AP Endo I; endodeoxyribonuclease (apurinic or apyrimidinic); deoxyribonuclease (apurinic or apyrimidinic). *E. coli* Endo III; phage-T4 UV endonuclease; *Micrococcus luteus* UV endonuclease; AP site-DNA 5'-phosphomonoester-lyase; and X-ray Endo III are examples of AP lyases. One unit of AP lyase is defined as the amount of enzyme required to cleave 1 pmol of a 34 mer oligonucleotide duplex containing a single AP site in a total reaction volume of 10 μl in 1 hour at 37° C. in 1× an optimal reaction buffer containing 10 pmol of fluorescently labeled oligonucleotide duplex. The AP site is created by treating 10 pmol of a 34 mer oligonucleotide duplex containing a single uracil residue with 1 unit of UDG for 2 minutes at 37° C.

The term "adaptor" refers to an at least partially double-stranded nucleic acid, typically composed of one or two oligonucleotides that can be ligated to at least one strand of a double-stranded DNA molecule. The double stranded part of an adaptor may be 10 to 150 bases in length, e.g., 40 to 120 bases, although adaptors outside of this range are envisioned.

The term "adaptor-tagged," as used herein, refers to a nucleic acid that has been tagged by, i.e., covalently linked with, an adaptor. An adaptor can be joined to a 5' end and/or a 3' end of a nucleic acid molecule.

The term "tagged DNA" as used herein refers to DNA molecules that have an added adaptor sequence, i.e., a "tag" of synthetic origin. An adaptor sequence can be added (i.e., "appended") by a transposase.

The term "hairpin adaptor" and "loop adaptor" refer to an adaptor that is in the form of a hairpin loop. In one embodiment, after ligation the hairpin loop can be cleaved to produce strands that have non-complementary tags on the ends. In some cases, the loop of a hairpin adaptor may contain a uracil residue, and the loop can be cleaved using UDG and Endo VIII.

The term "adaptor-ligated sample", as used herein, refers to a sample that has been ligated to an adaptor. As would be understood given the definitions above, a sample that has been ligated to an asymmetric adaptor contains strands that have non-complementary sequences at the 5' and 3' ends.

In some embodiments, the method comprises producing a reaction mix comprising a thermolabile UDG, an AP lyase and fragments of genomic or plasmid DNA that comprise one or more uracil residues. In some embodiments, the DNA fragments in the initial sample may be made by extracting genomic DNA or a plasmid from a biological sample, and then fragmenting it. In these embodiments, the initial steps may be done mechanically (e.g., by sonication, nebulization, or shearing) or using a double stranded DNA "dsDNA" fragmentase enzyme (New England Biolabs, Ipswich Mass.). In some of these methods (e.g., the mechanical and fragmentase methods), after the DNA is fragmented, the ends may be polished and A-tailed prior to ligation to an adaptor. Alternatively, the ends may be polished and ligated to adaptors in a blunt-end ligation reaction. In other embodiments, the DNA in the initial sample may already be fragmented (e.g., as is the case for FFPE samples and circulating cell-free DNA (cfDNA), e.g., ctDNA). The fragments in the initial sample may have a median size that is below 1 kb (e.g., in the range of 50 bp to 500 bp, or 80 bp to 400 bp), although fragments having a median size outside of this range (e.g., fragments that are at least 1 kb or at least 2 kb in length) may be used in some embodiments.

As noted above, the fragments comprise one or more uracil residues. In these embodiments, the uracil residues may be present in the fragments or at the ends of the fragments. In some embodiments, the uracil residues may be present in an oligonucleotide that has been incorporated into or ligated onto one or both ends of the fragments. In some embodiments, the uracil residues may be part of an adaptor that is ligated to at least one end of a genomic or plasmid fragment. In some embodiments, the adaptor may have a stem-loop structure in which the end of the stem is ligated onto the fragments. As described in U.S. Pat. No. 8,420,319, the loop of such an adaptor may contain a uracil residue. In these embodiments, cleavage of such an adapter at the uracil may produce ends that have non-complementary sequences.

The UDG used in the method may have an amino acid sequence that is at least 80% identical to (e.g., at least 85% identical to, at least 90% identical to, at least 95% identical to, at least 99% identical to, or the same as) a wild-type UDG from a psychrophilic organism, examples of which are encoded by the genomes of various species of the genera *Pseudoalteromonas, Arthrobacter, Psychrobacter, Halomonas, Pseudomonas, Hyphomonas*, and *Sphingomonas*. Exemplary wild-type UDG proteins are defined by the following accession numbers: YP341051.1, WP 024031570.1, WP 008136387.1, WP 004587991.1, WP 007376482.1, WP 002961393.1, WP 008170868.1, KDC52516.1, WP 007583745.1, WP 010553270.1, WP010391534.1, WP 008467778.1, WP 006793151.1, WP 016900536.1, WP 010556560.1, EWS 99431.1, YP 004069606.1, WP 016709899.1, and WP 008128988.1. Embodiments described herein may alternatively or additionally utilize commercially available thermolabile UDGs such as Antarctic UDG from New England Biolabs (Ipswich, Mass. Catalog # M0372S), Cod UDG (Cod UNG) from Atlantic Cod from ArcticZymes (Tromso, Norway), Thermolabile UDG from a marine bacterium from Enzymatics (Beverly, Mass.), UDG, heat-labile from marine bacterium BMTU 3346 from Roche (Indianapolis, Ind.) and HK™-UNG Thermolabile UDG from Epicenter (Stockholm, Sweden). The AP lyase may include any of *E. coli* Endo III, *E. coli* Endo VIII, Tma Endo III, and/or Tth Endo IV. In some embodiments, the AP lyase may be thermolabile.

After the reaction mix is made, the method may comprise incubating the reaction mix for a period of time (e.g., at least 10 minutes) at a temperature of below 40° C. to cleave the genomic or plasmid DNA fragments at the one or more uracil residues. This step of the method may comprise incubating the reaction mix for at least 10 minutes (e.g., at least 30 minutes) at a temperature in the range of 20° C. to 40° C. in order to cleave the fragments at the uracil residues. As noted above, in some embodiments, this step of the method may result in cleavage of a loop adaptor at one or more uracil residues to produce fragments that have ends that have non-complementary sequences. This allows those fragments to be efficiently amplified by polymerase chain reaction (PCR).

Next, the method may involve raising the temperature of the reaction mix to at least 50° C. (e.g., a temperature in the range of 50° C.-75° C.) for a period of time (e.g., for 2 to 30 minutes or more) to inactivate the thermolabile UDG.

After the UDG is inactivated the method comprises deaminating the fragments to convert any cytosine residues in the fragments to uracil. This may be done enzymatically (i.e., using a cytosine deaminase; see WO 2013/138644) or chemically (e.g., using sodium bisulfite; see Ehrich, Nucl. Acids Res. 35:e29 (2007)). The earlier inactivation step prevents the UDG from removing the uracil residues produced in the deamination step. If the deaminating is done enzymatically, then a cytosine deaminase may be used (see for example, U.S. Pat. No. 9,121,061) or other deaminase selected from the APOBEC family of deaminases), (Stenglein, Nature Structural & Molecular Biology, 17: 222-229 (2010)). In any embodiment, the deaminase used may have an amino acid sequence that is at least 90% identical to (e.g., at least 95% identical to) the amino acid sequence of GenBank accession number AKE33285.1, which is the human APOBEC3A. In these embodiments, deamination may be effected by adding the enzyme to the reaction mix, after the UDG has been inactivated. In some embodiments, the temperature of the reaction mix may be adjusted to the optimal temperature of the deaminase used (e.g., a temperature in the range of 30° C.-42° C.).

As would be apparent, the deaminated fragments can be amplified (by PCR) and sequenced. The deamination step converts C to U, but mC remains unchanged. When bisulfite-treated DNA is sequenced, unmethylated C is read as thymine (T), and mC is read as C, yielding single-nucleotide resolution information about the methylation status of a segment of DNA. The sequencing step may be done using any convenient next generation sequencing method and may result in at least 10,000, at least 50,000, at least 100,000, at least 500,000, at least 1M at least 10M at least 100M or at least 1B sequence reads. In some cases, the reads are paired-end reads. As would be apparent, the adaptors and/or the primers used for amplification may be compatible with use in any next generation sequencing platform in which primer extension is used, e.g., Illumina's reversible terminator method, Roche's pyrosequencing method (454), Life Technologies' sequencing by ligation (the SOLID® platform), Life Technologies' Ion Torrent™ platform or Pacific Biosciences' fluorescent base-cleavage method. Examples of such methods are described in the following references: Margulies, et al (Nature 2005 437: 376-80); Ronaghi, et al (Analytical Biochemistry 1996 242: 84-9); Shendure (Science 2005 309: 1728); Imelfort, et al (Brief Bioinform. 2009 10:609-18); Fox, et al (Methods Mol Biol. 2009; 553:79-108); Appleby, et al (Methods Mol Biol. 2009; 513:19-39) English (PLoS One. 2012 7: e47768) and Morozova (Genomics. 2008 92:255-64), which are incorporated by reference for the general descriptions of the methods and the particular steps of the methods, including all starting products, reagents, and final products for each of the steps. In some embodiments, the deaminated products may be sequenced using a long read single-molecule sequencing approach such as Nanopore sequencing (e.g. as described in Soni, et al Clin Chem 53: 1996-2001 2007, and developed by Oxford Nanopore Technologies) or Pacific Biosciences' fluorescent base-cleavage method (which currently have an average read length of over 10 kb, with some reads over 60 kb). Alternatively, the products may be sequenced using the methods of Moleculo (Illumina, San Diego, Calif.), 10× Genomics (Pleasanton, Calif.), or NanoString Technologies (Seattle, Wash.). In these methods, the sample is optionally diluted and then partitioned into a number of partitions (wells of a microtitre plate or droplets in an emulsion, etc.) in an amount that limits the probability that each partition does not contain two molecules of the same locus (e.g., two molecules containing the same gene). Next, these methods involve producing indexed amplicons of a size that is compatible with the sequencing platform being used (e.g., amplicons in the range of 200 bp to 1 kb in length) where amplicons derived from the same partitions are barcoded with the same index unique to the partition. Finally, the indexed amplicons are sequenced, and the sequence of the original, long, molecules can be reconstituted using the index sequences. Long range sequencing may also be done by using barcoded transposons (see, e.g., Adey, Genome Res. 2014 24: 2041-9 and Amini, Nat Genet. 2014 46: 1343-9), and by using the "reflex" system of Population Genetics Technologies (Casbon, Nucleic Acids Res. 2013 41:e112).

Reads are mapped to a reference sequence using an appropriate algorithm, for example, Bismark (see for example, Krueger et al. Bioinformatics 27, no. 11 (2011): 1571-1572) and the methylation status of a nucleotide can be called. See also WO 2017/075436 for a description of these methods. After sequencing, the method may comprise identifying the sites of methylcytosines and/or hydroxymethylcytosine residues in the fragments. This may be done by comparing the sequences obtained from the method to a reference sequence (e.g., sequences obtained from a second portion of the same sample that has not been deaminated).

Also provided are a variety of compositions used in the method. In some embodiments, a composition may comprise a thermolabile UDG, an AP lyase and fragments of genomic or plasmid DNA that contain one or more uracil residues, e.g., may comprise a loop or hairpin adaptor that is ligated to at least one end of the fragments. Descriptions of these components as well as other optional components that can be present in the composition are described above.

Alternative Embodiments

Also provided herein is a method for modifying an adaptor ligated to a fragment of genomic or plasmid DNA. In some embodiments, this method may comprise producing a reaction mix comprising a thermostable UDG (e.g., a UDG from a thermophile such as *T. thermophilus*, Tth or *A. fulgidus*, Afu), a thermostable AP lyase (e.g., an AP lyase from a thermophile such as Tth), ligase (e.g., a ligase such as T4 DNA ligase that is active at a temperature in the range of 15° C. to 30° C.), fragments of genomic or plasmid DNA, and an adapter such as a loop or hairpin adaptor containing one or more uracil residues. Next, the method comprises incubating the reaction mix at a temperature of below 37° C. (e.g., a temperature in the range of 14° C. to 25° C.) to ligate the adapter onto at least one end of the fragments of genomic or plasmid DNA. Finally, the method may comprise raising the temperature of the reaction mix to at least 50° C. for a period of time in order to activate the thermostable UDG and thermostable AP lyase, thereby cleaving the adapter at the one or more uracil residues.

This method has conventionally been done in multiple steps, e.g., by first ligating the fragments, then inactivating the enzymes used for ligation (e.g., by heating the reaction), and then performing a separate cleavage reaction in which the uracils in the adaptor are cleaved. In the present method, the reagents can be combined into a single tube, and the switch between the ligation and cleavage reactions is affected by simply raising the temperature of the reaction. In some embodiments, the method may further comprise deaminating the fragments after the UDG has been inactivated or separated away.

Also provided is a method for cleaving single strand DNA at a uracil where the single strand DNA is present in very low amounts because of the low amounts of target DNA to which it might be ligated if the single stranded DNA is an adaptor. Alternatively target DNA for methylation analysis may be present at very low amounts such as may occur in forensic applications or detection of pathogens. Where very low concentrations of target DNA occur, longer incubation periods may be desirable for reasons understood in the art (REF)

Embodiments of such a method may comprise: producing a reaction mix comprising UDG (which can be a thermolabile UDG or *E. coli* UDG, for example), Endo III and fragments of genomic or plasmid DNA that comprise an adapter containing one or more uracil residues, wherein the adaptor is ligated to at least one end of the fragment; and incubating the reaction mix to cleave the adaptor at the one or more uracil residues. As shown below, use of Endo III prevents substrate degradation over extended incubation periods and, as such, is used in preference to Endo VIII where long incubations may be performed. For example, the combination of UDG and Endo III may be used to cleave a strand of a DNA adaptor at a uracil where there is a limiting amount of DNA thus requiring a longer incubation period. In these embodiments, the initial sample of fragmented DNA may contain less than 200 ng of fragmented DNA, e.g., 10 pg to 200 ng, 100 pg to 200 ng, 1 ng to 200 ng or 5 ng to 50 ng, or less than 10,000 (e.g., less than 5,000, less than 1,000, less than 500, less than 100 or less than 10) haploid genome equivalents, depending on the genome. Use of Endo III instead of Endo VIII should reduce the number of degraded molecules, thereby allowing more molecules to be sequenced.

Kits

Also provided by the present disclosure are kits for practicing the subject method, as described above. In certain embodiments, a kit may comprise a thermolabile UDG or thermostable UDG, an AP lyase a deaminase and optionally an oligonucleotide containing one or more uracil residues ligated to at least one end of the fragments. In some embodiments, the oligonucleotide may be a loop or hairpin adaptor. The kit may alternatively comprise a thermostable UDG and Endo III. The components of the kit may be combined in one container, or each component may be in its own container. For example, the components of the kit may be combined in a single reaction tube or in one or more different reaction tubes. Further details of the components of this kit are described above. The kit may also contain other reagents described above and below that may be employed in the method, e.g., a buffer, ligase, controls, amplification primers, etc., depending on how the method is going to be implemented.

In addition to the above-mentioned components, the subject kit may further include instructions for using the components of the kit to practice the subject method. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The methods, compositions and kits described above can be employed to analyze genomic DNA and, in some cases, plasmids, from virtually any organism, including, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, where in certain embodiments the mammal is a human. In exemplary embodiments, the sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include blood, serum, plasma, saliva, mucous, phlegm, cerebral spinal fluid, pleural fluid, tears, lactal duct fluid, lymph, sputum, synovial fluid, urine, amniotic fluid, and semen. In particular embodiments, a sample may be obtained from a subject, e.g., a human. In some embodiments, the sample comprises fragments of human genomic DNA. In some embodiments, the sample may be obtained from a cancer patient. In some embodiments, the sample may be made by extracting fragmented DNA from a patient sample, e.g., a formalin-fixed paraffin embedded tissue sample. In some embodiments, the patient sample may be a sample of cell-free "circulating" DNA from a bodily fluid, e.g., peripheral blood e.g. from the blood of a patient or of a pregnant female. The DNA fragments used in the initial step of the method should be non-amplified DNA that has not been denatured beforehand. The DNA in the initial sample may be made by extracting genomic DNA from a biological sample, and then fragmenting it. However, as noted above, the DNA in the initial sample may already be fragmented.

All references cited herein are incorporated by reference.

EXAMPLES

Aspects of the present teachings can be further understood in light of the following examples, which should not be construed as limiting the scope of the present teachings in any way.

Example I: Preparation of Thermolabile Nicking Agents Specific for Uracil

Nicking agents cleave one strand of a duplex DNA. The artificial nicking agents used in these examples, include a cocktail of 2 or more enzymes where at least one of the enzymes in the cocktail is an N-glycosylase and at least one of the enzymes in the cocktail has AP-lyase or AP-endonuclease. Here the artificial nicking agents nick double-stranded DNA molecule at a non-standard nucleotide, generating a nucleotide gap and leaving a 5' phosphate and 3' phosphate at the nick location. In this example, nicking is achieved by thermolabile or thermostable nicking agents that include a thermolabile UDG and either Endo VIII or Endo III glycosylase/lyase.

Preparation of substrate for assaying thermolabile nicking agent activity: A double-stranded 34 mer oligonucleotide containing a single U at the 16th position and labeled by a 5' carboxyfluorescein (FAM) is shown in FIG. 1A. 10 µM of this labeled oligonucleotide was mixed with a slight excess (10%) of unlabeled complementary oligonucleotide (11 µM) containing adenine at the position opposite the uracil in a 200 µL volume and incubated for 2 minutes at 85° C. The mixture was gradually cooled down to room temperature to yield the double-stranded oligonucleotide.

Based on the activity unit definition of UDG glycosylase (one unit of UDG glycosylase activity was defined as the amount of enzyme that catalyzes the release of 60 pmol of uracil per minute from double-stranded, uracil containing DNA (New England Biolabs Catalog 2015-2016, p. 124), the amount of UDG required to prepare 1 unit of nicking agent was theoretically calculated to be 0.011 unit. However, the amount of this component in the nicking agent can vary, depending on the desirability of increasing the rate for release of uracil bases relative to the rate of nicking at abasic sites. Accordingly, the amount of UDG component in one activity unit of nicking agent can be increased at least 2-fold to 100-fold higher than the theoretically requisite minimum amounts, to a concentration of, for example 0.022 to 1.0 unit of UDG.

The optimal amount of the second component, Endo VIII or Endo III required to prepare 1 unit of the respective artificial nicking agent, Thermolabile UCR Enzyme, was determined as follows: Various amounts of Endo III (7.2 U to 0.45 U; 20 ng to 1.25 ng) or Endo VIII enzyme were pre-mixed with 0.2 units of Thermolabile UDG and the resulting mixtures were assayed for complete nicking of 10 pmol substrate in 15 minutes at 37° C. in 10 µL reaction buffer (50 mM potassium acetate, 20 mM Tris-acetate, 10 mM magnesium acetate, 100 µg/mL BSA, pH 7.9). The reactions were heat inactivated for 10 minutes at 65° C. and the products analyzed by capillary electrophoresis (see FIG. 2). The results of the activity assay showed that complete digestion of substrate occurred with at least 5 ng of Endo III in the presence of 0.2 units of Thermolabile UDG. According to the results of this example, 1 unit of thermolabile nicking agent can be prepared by mixing at least 1 unit of Endo III protein with 0.2 unit of UDG (FIG. 2).

One unit of activity of a thermolabile nicking agent was defined as having in the mixture, sufficient amounts of the individual components required to cleave to completion, 10 pmol of a 34-mer oligonucleotide duplex containing a single uracil paired with adenine in 10 µL of reaction buffer for 15 minutes at 37° C. The optimal ratio of components in the mixture for producing a nicking reagent was determined according to the unit definition (U.S. Pat. No. 7,435,572). Additionally, the nicking agent is completely heat inactivated at 65° C. for 10 minutes.

Thermolability of the AP endonuclease: 1 unit of the thermolabile nicking agent was incubated with 10 pmol of the 34 mer fluorescently labeled oligonucleotide duplex containing a single uracil base in 10 µL reaction buffer (50 mM potassium acetate, 20 mM Tris-acetate, 10 mM magnesium acetate, 100 µg/mL BSA, pH 7.9) and incubated for 15 minutes at 37° C. followed by heat inactivation for 10 minutes at 65° C. Following heat inactivation, the addition of 10 pmol of a 34 mer fluorescently labeled oligonucleotide duplex containing a single AP site was used to test whether residual AP Endonuclease activity occurred.

The extent of thermolability of both components (UDG and Endo VIII or Endo III) was then determined using capillary electrophoresis based detection of the fluorescently labeled oligonucleotide substrate and cleaved product. No additional cleavage of the fluorescently labeled oligonucleotide substrate was detected following heat inactivation of the thermolabile nicking agent for 10 minutes at 65° C.

Figure 3A:
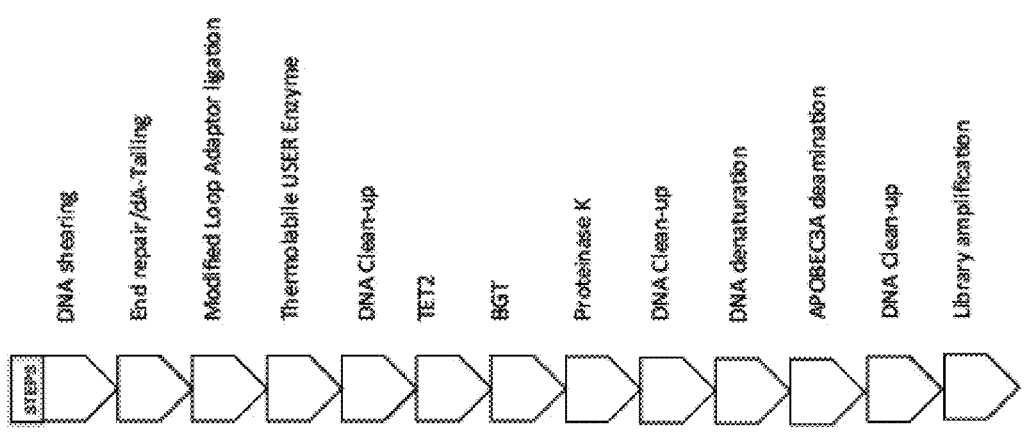
FIG. 3A and FIG. 3B schematically illustrate workflows in which a thermolabile nicking agent (i.e., a nicking agent composed of a thermolabile UDG and an AP lyase) may be employed.
Figure 3B:
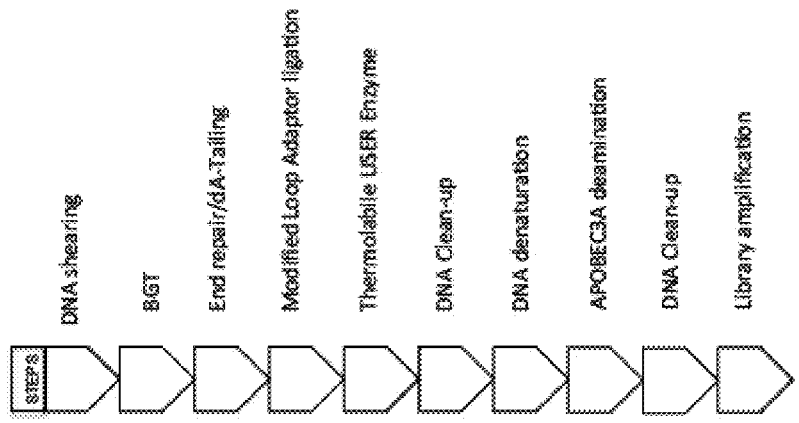

Example 2: Detection of 5-Methylcytosine and/or 5-Hydroxymethylcytosine in Mammalian Genomes In commercial nicking agents, E. coli UDG is only partially heat labile and has some residual activity after a DNA cleanup step and therefore can generate AP sites (apurinic/apyrimidinic site) in APOBEC3A deaminated DNA. This results in potential blocking of DNA polymerase activity in the subsequent PCR reaction. This example describes the usefulness of the heat labile nicking agent in the construction of genome libraries using the APOBEC-seq method (WO 2017/075436) for the detection of 5-methylcytosine and/or 5-hydroxymethyl cytosine in DNA. The workflow is shown in FIG. 3A and FIG. 3B.

5-methylcytosine in DNA was detected using a thermolabile nicking agent as follows: 50 ng of genomic DNA was sheared in 50 μL of 2 mM TRIS, pH 8.0, using Covaris S2. End repair and dA-tailing of sheared DNA fragments was achieved using the NEBNext® Ultra™ II DNA Library Prep Kit (New England Biolabs, Ipswich, Mass.). An NEBNext adaptor was ligated to dA-tailed DNA in the presence of or before addition of the thermolabile nicking agent, where the thermolabile nicking agent contained an effective concentration ratio of components exemplified in the figures. Where the nicking agent is added after the ligase reaction, the ligation reaction proceeds for 15 minutes with the loop adaptor (NEBNext loop adaptor) before addition of the nicking agent.

For methylcytosine detection, modified cytosines were then oxidized by TET2, glucosylated by T4 β-glucosyltransferase (BGT) and treated with proteinase K. The temperature of the reaction mixture was subsequently raised to 80° C. to inactivate the nicking agent. Deamination was carried out using APOBEC3A according to the instructions of the manufacturer (New England Biolabs, Ipswich, Mass.). Amplification followed, the samples cleaned up using AMPure® beads (Beckman Coulter, Brea, Calif.) and then sequenced using an Illumina sequencer.

5-hydroxymethylcytosine in DNA was detected using a thermolabile nicking agent as follows: 50 ng of genomic DNA was sheared in 50 μL of 2 mM TRIS, pH 8.0, using Covaris S2. The DNA was then glucosylated using BGT according to manufacturer instructions (New England Biolabs, Ipswich, Mass.). End repair and dA-tailing on sheared DNA fragments was achieved using the NEBNext Ultra II DNA Library Prep Kit. An NEBNext adaptor was ligated to dA-tailed DNA in the presence of or before addition of the thermolabile nicking agent, where the thermolabile nicking agent contained an effective concentration ratio of components exemplified in the figures. Where the nicking agent is added after the ligase reaction, the ligation reaction proceeds for 15 minutes with the loop adaptor (NEBNext loop adaptor) before addition of the nicking agent. The DNA was purified with AMPure bead purification (1.0× volume) after proteinase K treatment, deaminated using APOBEC 3A, amplified and sequenced using an Illumina sequencer.

Example 3: Preparation of Thermostable Artificial Nicking Agents Specific for Uracil The assay utilized an oligonucleotide shown in FIG. 1B. Where one unit of UDG glycosylase activity was defined as the amount of enzyme that catalyzes the release of 60 pmol of uracil per minute from double-stranded, uracil containing DNA (New England Biolabs Catalog 2015-2016, p. 124), the amount of UDG required to prepare 1 unit of artificial nicking agent was theoretically calculated to be 0.011 unit. However, the amount of this component in one activity unit of nicking agent can be increased at least 2-fold to 100-fold higher than the theoretically requisite amounts, to a concentration of, for example 0.022 to 1.0 unit of UDG to increase the rate of release of uracil.

Figure 4:
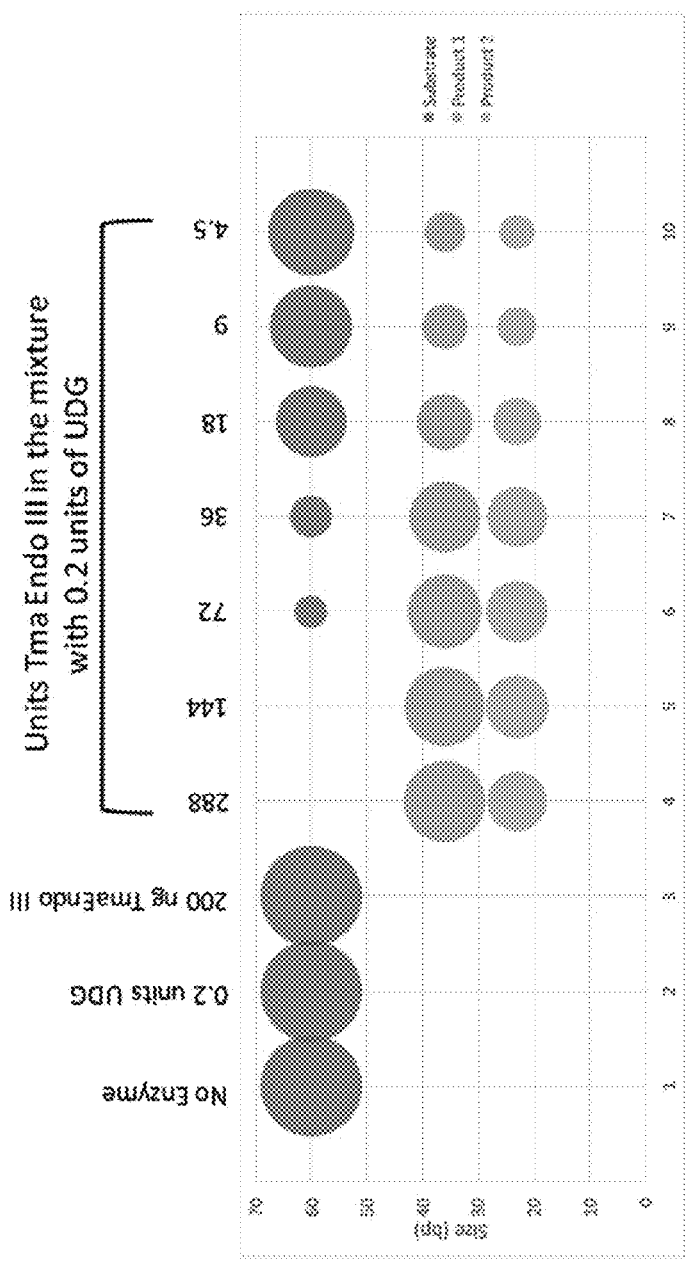
FIG. 4 shows results of thermostable UDG (Afu UDG) and a thermostable lyase (Tma Endo III). The optimal amount of Tma Endo III glycosylase/AP lyase in a nicking agent can be determined in a mixture with Afu UDG glycosylase in order to produce a thermostable nicking agent. The assay utilizes a substrate having a sequence shown in FIG. 1B. 2-fold serially diluted amounts of Tma Endo III varying in the range from 288-4.5 U were pre-mixed with 0.2 unit of Afu UDG glycosylase and assayed for complete nicking of 10 pmol of substrate for 15 minutes at 65° C. Lane 1 (shown on the far left) is a control showing the substrate without enzyme treatment. Neither Afu UDG alone (shown in lane 2, second from the left) or Tma Endo III alone (shown in lane 3, third from the left) is capable of nicking substrate containing uracil, but the mixtures containing 0.2 units of Afu UDG and at least 144 U of Tma Endo III yield complete nicking of 10 pmol of substrate (lanes 4-10). Mixtures containing 72 U or less of Tma Endo III are only partially digested (lanes 6-10). These data show that in order to obtain complete digestion under the conditions used, the Tma Endo III: Afu UDG unit ratio should be at least about 80 (Endo IV): 0.2 (UDG), i.e., 400:1.

An amount of Tma Endo III (New England Biolabs, Ipswich, Mass.) in 1 unit of a thermostable nicking agent (Afu UDG) was determined as follows: Tma Endo III protein (288 U to 4.5 U; 200 ng to 3.125 ng) were pre-mixed with 0.2 units of Afu UDG and the resulting mixtures were assayed for complete nicking of 10 pmol substrate in 15 minutes at 65° C. in 10 μL reaction buffer (20 mM Tris-HCl, pH 8.8, 10 mM $(NH_4)_2SO_4$, 10 mM KCl, 2 mM $MgSO_4$, 0.1% Triton X-100). The reactions were quenched by the addition of equal volume of formamide and the products were analyzed using capillary electrophoresis. The results of the activity assay showed that complete digestion of substrate occurred with at least 144 U Tma Endo III in the presence of 0.2 units of Afu UDG (FIG. 4). The results in FIG. 4 show that 1 unit of thermostable nicking agent can include at least about 80 units of Tma Endo III protein with 0.2 unit of Afu UDG. The thermostable nicking agent (0.2 U UDG: 144 U Tma Endo III) can completely cleave 10 pmol of dU-containing substrate in 15 minutes at 65° C. in 10 μL reaction buffer (20 mM Tris-HCl, pH 8.8, 10 mM $(NH_4)_2SO_4$, 10 mM KCl, 2 mM $MgSO_4$, 0.1% Triton X-100).

Figure 5:
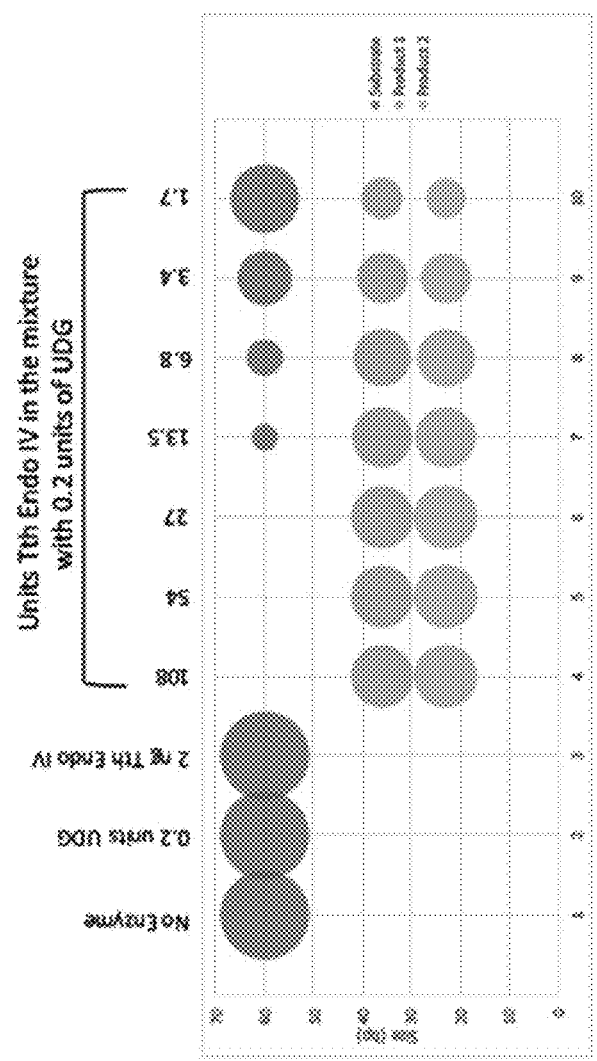
FIG. 5 shows results of a thermostable UDG (Afu UDG) and a thermostable lyase (Tth Endo IV). The optimal amount of Tth Endo IV glycosylase/AP lyase can be determined in a mixture with Afu UDG glycosylase in order to produce a thermostable nicking agent. The assay utilizes a substrate having a sequence shown in FIG. 1B. 2-fold serially diluted amounts of Tth Endo IV varying in the range from 108-1.7 U were pre-mixed with 0.2 unit of Afu UDG glycosylase and assayed for complete nicking of 10 pmol of substrate for 15 minutes at 65° C. Lane 1 (on the far left) is a control showing the substrate without enzyme treatment. Neither Afu UDG alone (shown in lane 2, second from the left) or Tth Endo IV alone (shown in lane 3, third from the left) is capable of nicking substrate containing uracil, but the mixtures containing 0.2 units of Afu UDG and at least 27 U of Tth Endo IV yield complete nicking of 10 pmol of substrate (lanes 4-6). Mixtures containing 13.5 U or less of Tth Endo IV are only partially digested (lanes 7-10). These data show that in order to obtain complete digestion under the conditions used, the Tth Endo IV: Afu UDG unit ratio should be at least about 15 (Endo IV): 0.2 (UDG), i.e., 75:1.

A similar effect is observed using a thermostable Endo IV with a thermostable UDG. Using the approach described above for Tma Endo III, 1 unit of nicking agent was identified as at least 27 U of Tth Endo IV protein with 0.2 unit of Afu UDG (FIG. 5). This mixture (0.2 U UDG: 27 U (0.5 ng) Tth Endo IV) could completely cleave 10 pmol of dU-containing 34-mer duplex substrate containing a single uracil paired with adenine in 15 minutes at 65° C. in 10 μL reaction buffer (20 mM Tris-HCl, pH 8.8, 10 mM $(NH_4)_2SO_4$, 10 mM KCl, 2 mM $MgSO_4$, 0.1% Triton X-100).

Figure 6A:
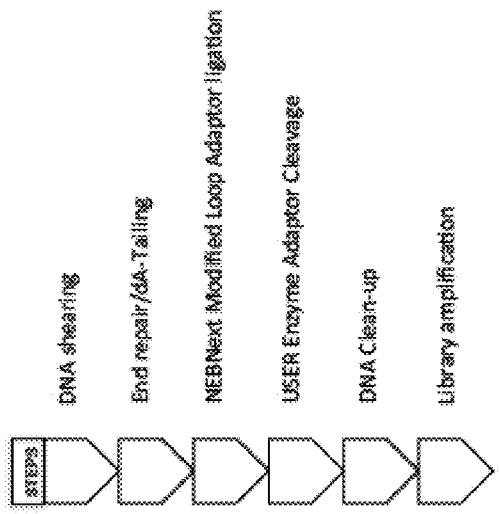
FIG. 6A and FIG. 6B schematically illustrate workflows in which a thermostable nicking agent (i.e., a nicking agent composed of a thermostable UDG and a thermostable AP lyase) may be employed.
Figure 6B:
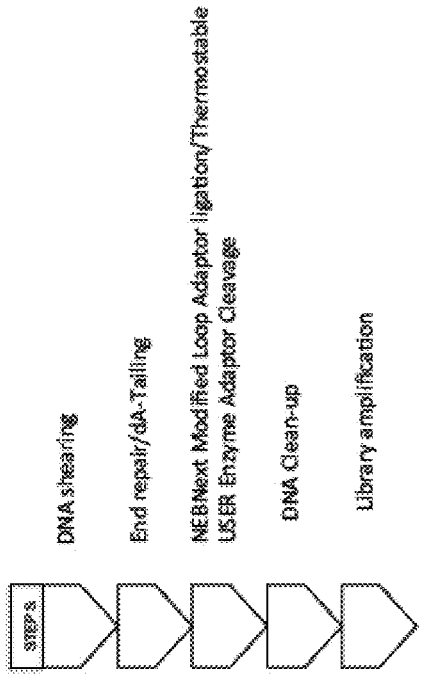
Figure 7:
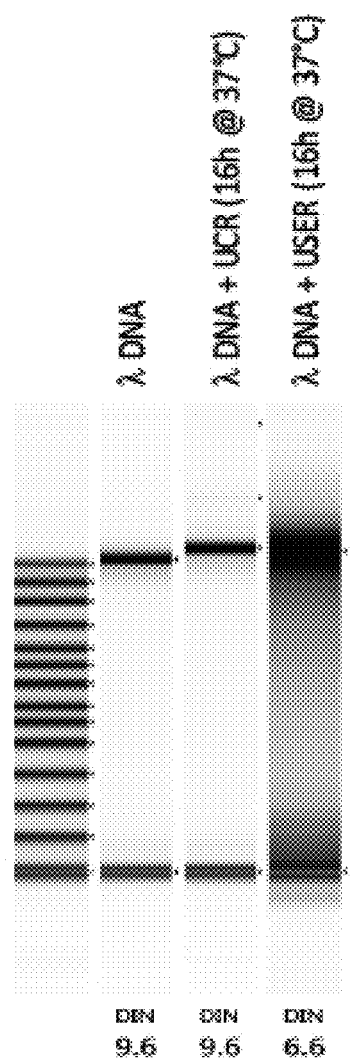
FIG. 7 shows an advantage of Endo III where Endo III provides specific cleavage at AP sites after 16 hours of incubation at 37° C. compared with Endo VIII using reaction conditions described in FIG. 2A which can cleave substrate non-specifically with long incubations. The extent of λ DNA (1 µg) degradation was tested by incubating 1 unit of nicking agent UDG+Endo III (*E. coli*) or UDG+Endo VIII (*E. coli*) for 16 hours at 37° C. followed by analysis using the Genomic DNA Analysis ScreenTape and Tape Station System (Agilent, Santa Clara, Calif.). As indicated by the DNA Integrity Number (DIN), no DNA degradation is observed after 16 hours incubation with UDG/Endo III (lane 2, DIN=9.6) as compared to the λ DNA control (lane 1, DIN=9.6), whereas a significant amount of DNA degradation has occurred after 16 hours incubation with UDG/Endo VIII (lane 3, DIN=6.6).

Example 4: Combination of Adaptor Ligation and Nicking in a Single Reaction Step in Next Generation Sequencing Library Preparation Exemplary workflows for using thermostable nicking enzymes are shown in FIGS. 3A, 3B, 6A and 6B. In particular, FIG. 6B provides a workflow in which adaptor ligation and nicking occur in a single reaction step in next generation sequencing library preparation. Since the thermostable nicking agent displayed no activity on dU containing substrates at 20° C. but is active at increased temperatures (65° C.), the reagents for the adaptor ligation and cleavage steps are combined and temperature controlled for example, by performing ligation for 15 minutes at 20° C. and then increasing the temperature to 65° C. for 15 minutes (adaptor cleavage by thermostable nicking agent).

Example 5: Combination of Adaptor Ligation and Nicking in a Single Reaction Step in Next Generation Sequencing Library Preparation Assay for non-specific cleavage by nicking agent after overnight incubation with substrate DNA nicking agent: 5 ng of Endo III protein was combined with 0.2 unit of UDG (E. coli UDG or a thermolabile UDG) to provide 1 unit of nicking agent. This mix was incubated with 1 μg of λ DNA in 50 μL reaction buffer (50 mM Tris-HCl, pH 7.5, 10 mM $MgCl_2$, 10 mM DTT, 1 mM ATP) for 16 hours at 37° C. The extent of λ DNA degradation was analyzed using the Genomic DNA Analysis screen tape system (Agilent, Santa Clara, Calif.). The results are shown in FIG. 2. In the presence of Endo III/UDG (UCR) no degradation of substrate was observed after 16 hours of incubation whereas significant degradation was found with Endo VIII/UDG.

It will also be recognized by those skilled in the art that, while the invention has been described above in terms of preferred embodiments, it is not limited thereto. Various features and aspects of the above described invention may be used individually or jointly. Further, although the invention has been described in the context of its implementation in a particular environment, and for particular applications those skilled in the art will recognize that its usefulness is not limited thereto and that the present invention can be beneficially utilized in any number of environments and implementations where it is desirable to examine analytes. Accordingly, the claims set forth below should be construed in view of the full breadth and spirit of the invention as disclosed herein.

What is claimed is:

1. A method for performing multiple enzyme reactions in a single tube, comprising:
   (a) producing a reaction mix comprising a thermolabile uracil-DNA glycosylase (UDG), a DNA-(apurinic or apyrimidinic site) lyase (AP-lyase) and fragments of genomic or plasmid DNA that comprise one or more uracil residues;
   (b) incubating the reaction mix at a temperature of below 40° C. to cleave the genomic or plasmid DNA fragments at the one or more uracil residues;
   (c) raising the temperature of the reaction mix to at least 50° C. for a period of time to inactivate the thermolabile UDG; and
   (d) after step (c) deaminating the fragments of genomic or plasmid DNA, thereby converting any cytosine in the fragments of genomic or plasmid DNA to uracil.

2. The method of claim 1, wherein the fragments of genomic or plasmid DNA comprise an oligonucleotide, and wherein the oligonucleotide comprises the one or more uracil residues.

3. The method of claim 2, wherein the oligonucleotide is an adapter ligated to at least one end of the genomic or plasmid fragments.

4. The method of claim 3, wherein the adaptor is a loop adaptor.

5. The method of claim 1, wherein AP lyase is also thermolabile.

6. The method of claim 1, wherein AP lyase is Endonuclease III.

7. The method of claim 1, wherein the deaminating is performed using a deaminase enzyme.

8. The method of claim 7, wherein the deaminase enzyme has at least 90% sequence identity with SEQ ID NO:1 (APOBEC).

9. The method of claim 1, wherein the deamination is performed by sodium bisulfite treatment.

10. The method of claim 1, further comprising (e) amplifying the fragments of genomic or plasmid DNA.

11. The method of claim 10, further comprising sequencing the amplification products.

12. The method of claim 11, further comprising identifying the sites of methylcytosines and/or hydroxymethylcytosine residues in the fragments of genomic or plasmid DNA.

* * * * *

SEQUENCE LISTING

```
<160> NUMBER OF SEQ ID NOS: 4

<210> SEQ ID NO 1
<211> LENGTH: 34
<212> TYPE: DNA
<213> ORGANISM: Artificial Sequence
<220> FEATURE:
<223> OTHER INFORMATION: Synthetic construct

<400> SEQUENCE: 1
gatttcattt ttattuataa ctttacttat attg                                 34

<210> SEQ ID NO 2
<211> LENGTH: 34
<212> TYPE: DNA
<213> ORGANISM: Artificial Sequence
<220> FEATURE:
<223> OTHER INFORMATION: Synthetic construct

<400> SEQUENCE: 2
ctaaagraaa aataaatatt gaaatgaata taac                                 34

<210> SEQ ID NO 3
<211> LENGTH: 56
<212> TYPE: DNA
<213> ORGANISM: Artificial Sequence
<220> FEATURE:
<223> OTHER INFORMATION: Synthetic construct

<400> SEQUENCE: 3
cggaattcgt ctaggtttga ggtugacatc ggatggtacc tcgagggcaa tgtcta         56

<210> SEQ ID NO 4
<211> LENGTH: 60
<212> TYPE: DNA
<213> ORGANISM: Artificial Sequence
<220> FEATURE:
<223> OTHER INFORMATION: Synthetic construct

<400> SEQUENCE: 4
gccttaagca gatccaaact ccaactgtag cctaggtacc atggagctcc cgttacagat     60
```